United States Patent [19]

Elgas

[11] Patent Number: 5,609,632
[45] Date of Patent: Mar. 11, 1997

[54] METHOD OF FABRICATING AN ARTIFICIAL LUNG

[75] Inventor: Roger J. Elgas, Anaheim Hills, Calif.

[73] Assignee: Medtronic, Inc., Minneapolis, Minn.

[21] Appl. No.: 618,474

[22] Filed: Mar. 18, 1996

[51] Int. Cl.⁶ ........................................... A61F 2/04
[52] U.S. Cl. .................... 623/12; 428/15; 427/2.24; 422/45; 422/48; 623/1; 623/9; 623/11; 128/898
[58] Field of Search ........................... 623/1, 3, 8, 9, 623/11, 12, 66, 901; 428/15, 16; 434/262, 265, 267, 268, 272, 295, 296, 297; 427/2.24, 2.25, 4; 424/3, 9, 422, 423, 424, 425, 426, 428, 434; 422/40, 41, 42, 44, 45, 46, 47, 48, 49; 156/653; 128/898

[56] References Cited

U.S. PATENT DOCUMENTS

| | | | |
|---|---|---|---|
| 3,708,071 | 1/1973 | Crowley | 210/321 |
| 4,205,059 | 5/1980 | Von Hagens | 427/4 |
| 4,244,992 | 1/1981 | Von Hagens | 428/15 |
| 4,371,686 | 2/1983 | Yamamoto et al. | 528/76 |
| 4,490,423 | 12/1984 | Gould et al. | 428/36 |
| 4,528,343 | 7/1985 | Kira | 528/26 |
| 4,543,063 | 9/1985 | Cohen | 433/175 |
| 4,698,207 | 10/1987 | Bringham et al. | 422/46 |
| 4,876,066 | 10/1989 | Bringham et al. | 422/46 |
| 5,162,102 | 11/1992 | Nogawa et al. | 422/48 |
| 5,338,512 | 8/1994 | Mathewson et al. | 422/46 |
| 5,447,724 | 9/1995 | Helmus et al. | 424/426 |
| 5,522,896 | 6/1996 | Prescott | 623/16 |

*Primary Examiner*—John G. Weiss
*Assistant Examiner*—Francis K. Cuddihy
*Attorney, Agent, or Firm*—Harry G. Weissenberger

[57] ABSTRACT

An artificial lung is created by taking an animal lung, filling either its circulatory system or its respiratory system with a hardenable liquid, hardening the liquid, then dissolving the natural lung tissue, coating the hardened liquid with a material forming a gas permeable membrane, removing the hardenable fluid, and enclosing the resulting artificial lung structure in a fluid-tight pouch.

10 Claims, 4 Drawing Sheets

5,609,632

METHOD OF FABRICATING AN ARTIFICIAL LUNG

FIELD OF THE INVENTION

This invention relates to artificial lungs, and more specifically, to a method of making an implantable oxygenator of a size and oxygenation capacity comparable to a human lung.

BACKGROUND OF THE INVENTION

Oxygenators, which substitute for a patient's lungs during, e.g., open heart surgery, have long been known. Conventionally, such oxygenators work by flowing the patient's blood across a bundle of hollow microporous fibers. Oxygen is pumped through the interior of the fibers, and a gas exchange takes place along the surface of the fibers. Just like in a living lung, oxygen migrates from the fiber interior into the blood, and carbon dioxide migrates from the blood into the fibers.

One problem with currently known oxygenators is that they are vastly less efficient than a natural lung. Conventional oxygenators typically have a blood-oxygen interface surface of about 2 $m^2$, whereas an adult human lung has an interface surface of about 70 $m^2$. With pure oxygen and an anesthetized, perfectly still patient, the 2 $m^2$ surface is sufficient, but it could not sustain life in ordinary air or in an active patient.

Sufferers from emphysema or other lung-damaging diseases would be greatly helped if it were possible to produce an implantable artificial lung with sufficient gas-blood interface area to allow the patient to function in a normal environment. The current fiber technology is not suitable for this purpose because it would require a fiber bundle so large that it could not be implanted and would require an inordinate amount of blood to prime. Consequently, an entirely new departure is needed in the art to create an artificial lung of manageable size yet with an interface surface area approximating that of a natural lung.

The reason why a natural lung has so much interface surface area is that the natural lung is composed of millions of microscopic generally spherical air-containing alveolar sacs whose membrane-like walls are perfused with capillaries through which the blood flows. Imitating that structure with artificially manufactured devices is not practical.

SUMMARY OF THE INVENTION

The present invention provides a novel approach to the above-described fabrication problem. Specifically, the inventive process involves taking a lung from a slaughtered animal such as a cow or a pig, replacing the blood in its capillaries with a reversibly hardenable liquid, hardening the liquid, and chemically dissolving the lung tissue. The resulting structure, which is essentially a three-dimensional negative of the capillary network, is then coated with a fine membrane of a gas permeable material to reconstitute the capillary network in a durable, aseptic form. Finally, the hardenable liquid is re-liquified and drained from the reconstituted capillaries. The artificial lung so produced can then be implanted in a patient and connected by conventional surgical techniques to the patient's circulatory and respiratory systems.

In another embodiment of the invention, the alveolar sacs themselves, rather than the capillaries, may be filled with a reversibly hardenable fluid to produce a negative replica of the lung's air passages which can be coated with a gas permeable material after the lung tissue is dissolved. The resulting artificial lung would have substantially less interface surface area but would be easier to fabricate.

DESCRIPTION OF THE PREFERRED EMBODIMENT

The detailed description set forth below in connection with the appended drawings is intended as a description of the presently preferred embodiments of the invention, and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
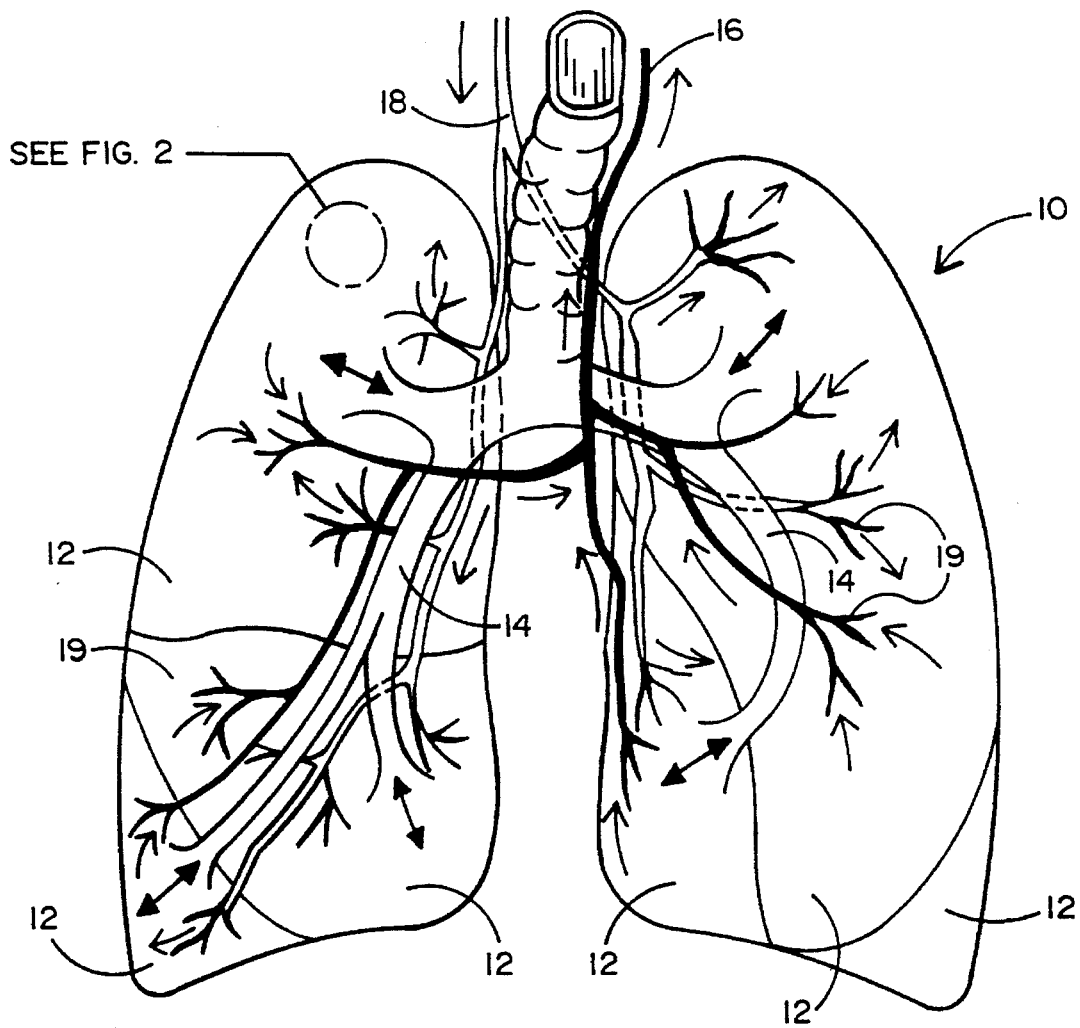
FIG. 1 is an overall view of a human lung.

The raw material for the artificial lung of this invention is an animal lung which can be readily obtained from meat processing plants. As shown in FIG. 1, a typical lung 10 may have several lobes 12, each of which is connected to the respiratory tract by a bronchus 14, and to the circulatory system by a pulmonary vein 16 and a pulmonary artery 18.

The fact that lungs tend to have several independent lobes 12 is useful in that artificial lungs of various sizes may be produced by using one or more lobes 12 separately, instead of the whole lung 10.

Figure 2:
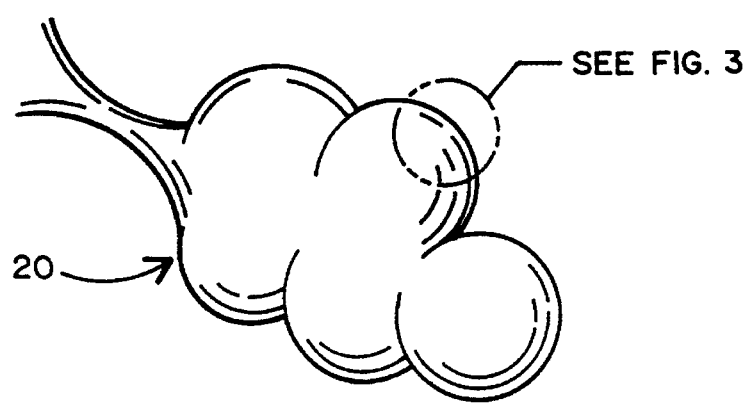
FIG. 2 is a detail section of an alveolar sac per line 2—2 of FIG. 1.
Figure 3:
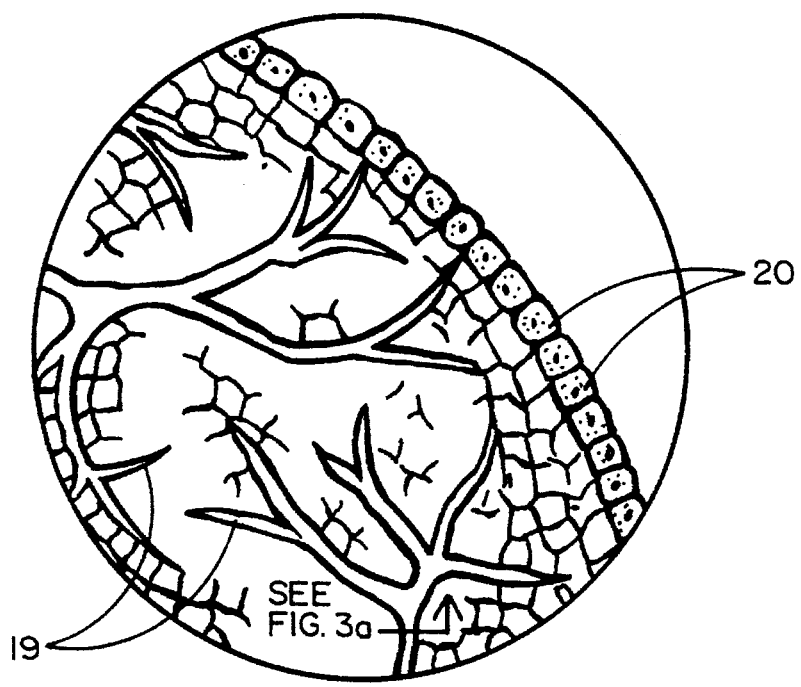
FIG. 3a–f are detail sections of a capillary during successive stages in the fabrication of the artificial lung of this invention.
Figure 3A:
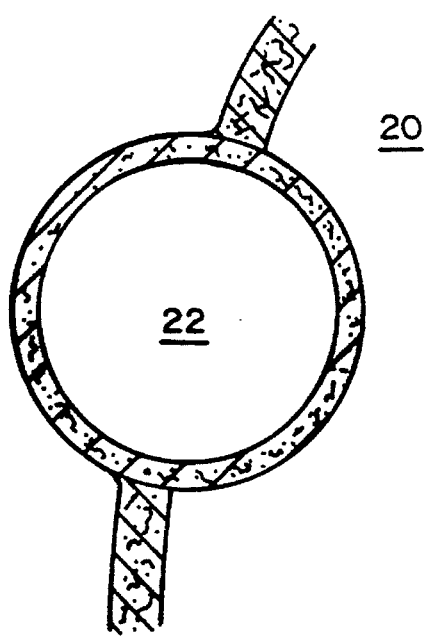

Inside the lung 10, the bronchus. 14 branches out to a large number of terminal bronchioles 19 which supply air to alveolar sacs 20 (FIG. 2). The walls of the alveolar sacs are perfused with capillary blood vessels 22 (FIG. 3a) connected to the pulmonary vein 16 and the pulmonary artery 18. Gas exchange between the blood and the air takes place through the walls of the capillaries 22 and of the alveolar sacs 20.

The objective of the present invention is to fabricate an artificial lung which is essentially identical in physical structure to the raw material animal lung but is composed of a durable, biocompatible material capable of forming a gas permeable membrane through which gas exchange can take place.

Figure 3B:
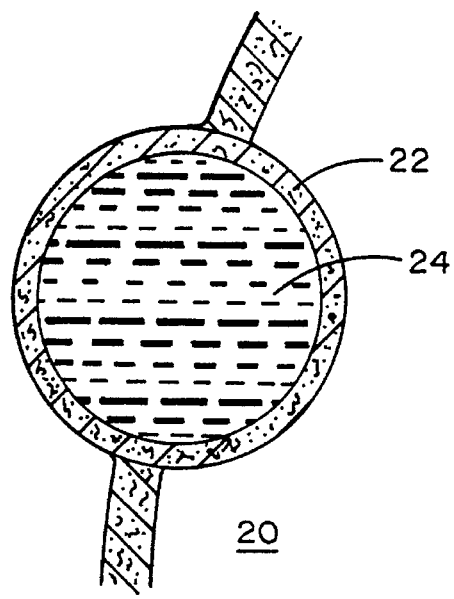
Figure 3C:
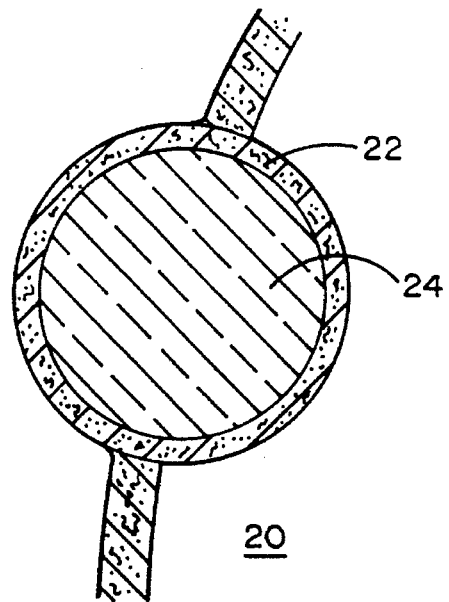

The inventive process, whose successive steps are illustrated in FIGS. 3a–f, begins by connecting the pulmonary vein 16 and the pulmonary artery 18 to an external circulation system (not shown) which washes out all blood from the capillaries 22 (FIG. 3a) and substitutes therefor a reversible, hardenable liquid 24 (FIG. 3b). The liquid 24 may be any suitable liquid of low viscosity which hardens and liquifies under circumstances (i.e. temperatures) that are not injurious to the animal lung tissue. The liquid 24 must also, when hardened, be impervious to attack by tissue-dissolving chemicals such as hydrogen peroxide. As a matter of example, a suitable liquid for this purpose would be gelatin. When all the capillaries 22 have been filled with the liquid 24, the liquid 24 is hardened (FIG. 3c). This is most conveniently accomplished by simply lowering the temperature of the lung 10 to a level below the melting point of the liquid 24.

The lung 10 is now immersed in a bath 25 of an appropriate chemical to dissolve the tissue 26 of lung 10 without attacking the hardened liquid 24. The result of this immersion is in essence a casting of the capillary system of the lung 10 (FIG. 3d).

Figure 3D:
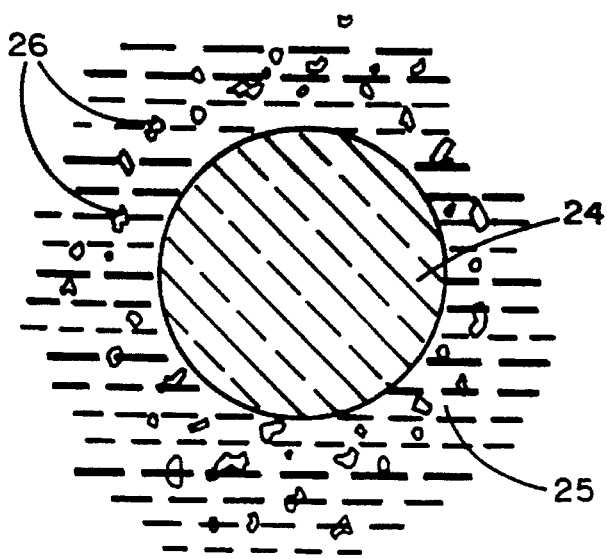
Figures 3E, 3F:
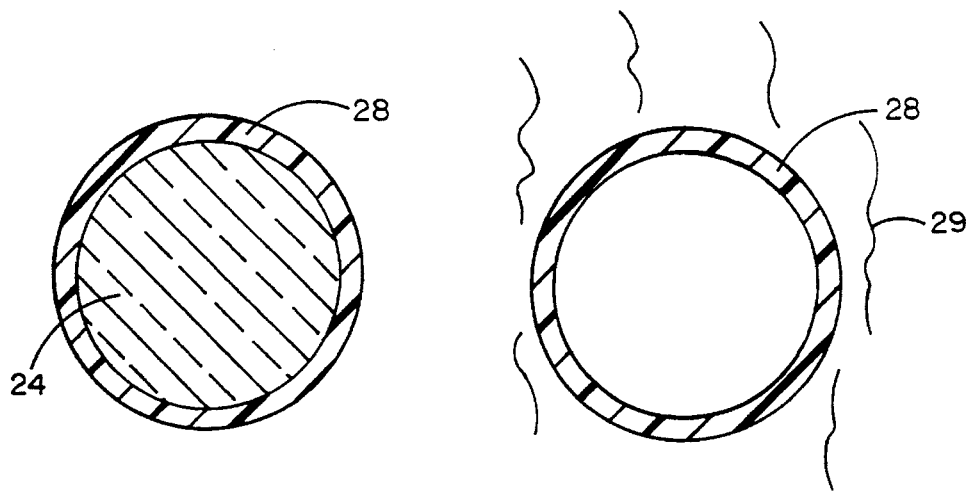

As shown in FIG. 3e, the capillary castings of FIG. 3d are now coated with a thin membrane 28 of a gas permeable biocompatible material. Any of the biocompatible polymers conventionally used in the manufacture of oxygenator gas exchange fibers would be suitable for this purpose. The hardened liquid 24 can then be re-liquefied (e.g. by raising the temperature as indicated by 29 in FIG. 3f) and washed out of what is now a durable, biocompatible, operational reproduction of the entire circulatory system of the lung 10.

Figure 4:
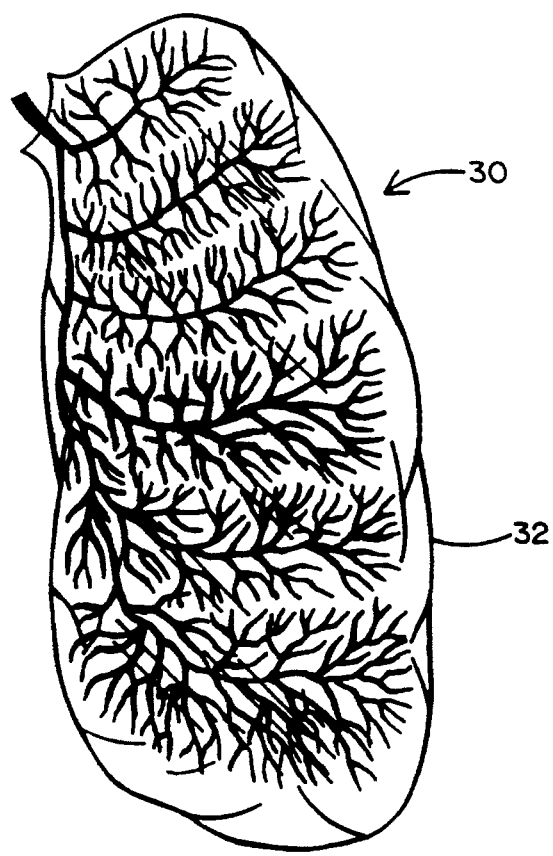
FIG. 4 is an elevational view of the artificial lung of this invention in its air supply sac.

The resulting structure 30 (FIG. 4) can now be enclosed in an airtight, liquid-impervious pouch 32. To implant the artificial lung 34 of this invention in a patient, the pouch 32 is surgically connected to the patient's respiratory system through one of the patient's bronchi, while the venal and arterial ends of the structure 30 are surgically connected to the patient's pulmonary vein and pulmonary artery, respectively.

By providing a physical structure which is essentially a duplicate of a natural lung, the artificial lung of this invention becomes in effect an implantable oxygenator with a gas-blood interface surface area comparable to that of the patient's own lungs. This makes it possible not only to sustain life without external assistance but to restore the ability to withstand strenuous exercise to patients suffering from lung impairments.

The creation and removal of a hardened filler for the blood vessels can be achieved by a number of different methods. For example, in addition to the temperature-related process described above, it would be possible to fill the blood vessels with urethane, cure the urethane, dissolve the tissue, coat the urethane structure with acid-resistant silicon rubber, and then etch the urethane away with acid. Alternatively, the blood vessels may be filled with a hardenable metallic salt, which could eventually be removed by electroplating it out through the blood vessels onto an electrode external of the lung.

An alternative embodiment of the invention involves making a casting not of the capillary system, but of the alveolar sacs 20 of the lung 10. Because the alveolar sacs 20 are considerably larger than the capillaries 22, the membrane 28 in the steps of FIG. 3e can be formed more reliably. On the other hand, the total surface area of the alveolar sacs 20 of the lung 10 is substantially less than that of the capillaries 22 but still much greater than the gas-blood interface surface area achievable with conventional oxygenation.

In the alternative embodiment, an appropriate fluid (e.g. t-butyl alcohol, whose melting point is 25.5° C., and whose boiling point is 82.8° C.) could be introduced into the lung 10 through the bronchus 14 in gaseous form and allowed to condense into a liquid filling the lung 10. The lung 10 can then be cooled to below 25.5° C. so that the t-butyl alcohol hardens. After that, the dissolving and coating steps of FIGS. 3d and 3e can be carried out as described above, and the t-butyl alcohol can then be liquified and evaporated to remove it from the structure created in the step of FIG. 3e. In that embodiment of the invention, implantation would require the structure 30 to be connected to the patient's bronchus and the pouch 32 to be connected to the patient's pulmonary vein and artery for blood circulation therethrough.

It is understood that the exemplary artificial lung described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

What is claimed is:

1. A method of making an implantable artificial lung, comprising the steps of:
    a) introducing into cavities of a natural lung a reversibly hardenable fluid;
    b) hardening said fluid;
    c) dissolving the tissue of said natural lung while said fluid is hardened;
    d) coating said hardened fluid with a material forming a gas permeable membrane; and
    e) removing said hardenable fluid from said gas permeable membrane.

2. The method of claim 1, in which said fluid is reversibly hardenable, and said hardening is reversed following said coating of said hardened fluid.

3. The method of claim 1, in which said hardenable fluid is acid-soluble when hardened, and said gas permeable membrane material is acid-resistant, said hardened fluid being removed from said gas permeable membrane by acid etching.

4. The method of claim 3, in which said hardenable fluid is urethane, and said gas permeable membrane material is silicone rubber.

5. The method of claim 1, in which said hardenable fluid is a metallic salt, and said hardened fluid is removed from said membrane by electrolysis.

6. The method of claim 1, further comprising the step of enclosing said gas permeable membrane in a fluid-tight pouch.

7. The method of claim 1, in which said cavities are a circulatory system of said natural lung.

8. The method of claim 1, in which said cavities are a respiratory system of said natural lung.

9. The method of claim 1, in which said reversibly hardenable fluid is a liquid.

10. The method of claim 1, in which said dissolving is done by a dissolving chemical, and said hardenable fluid is substantially impervious to said dissolving chemical when said hardenable fluid is hardened.

* * * * *

UNITED STATES PATENT AND TRADEMARK OFFICE
CERTIFICATE OF CORRECTION

PATENT NO. : 5,609,632
DATED : March 11, 1997
INVENTOR(S) : Roger J. Elgas

It is certified that error appears in the above-identified patent and that said Letters Patent is hereby corrected as shown below:

Column 2 line 42,"bronchus." should read --bronchus--.

Column 4, line 39, after "membrane", please insert --material--.

Signed and Sealed this

Twenty-second Day of May, 2001

Attest:

NICHOLAS P. GODICI

*Attesting Officer*   *Acting Director of the United States Patent and Trademark Office*